United States Patent [19]

Takehana

[11] Patent Number: 5,814,512
[45] Date of Patent: Sep. 29, 1998

[54] MICROORGANISM HAVING ALL THE IDENTIFYING CHARACTERISTICS OF ABSIDA FERM BP-4599 FOR PRODUCING PURPUROGALLIN DERIVATIVES

[75] Inventor: Yuki Takehana, Fujisawa, Japan

[73] Assignee: Hoffmann-La Roche Inc., Nutley, N.J.

[21] Appl. No.: 800,140

[22] Filed: Feb. 13, 1997

Related U.S. Application Data

[62] Division of Ser. No. 429,457, Apr. 27, 1995, Pat. No. 5,650,439.

[30] Foreign Application Priority Data

May 2, 1994 [EP] European Pat. Off. .............. 94106823

[51] Int. Cl.⁶ .............................. C12N 1/14; C12P 7/26; C12P 7/02; C07C 59/76
[52] U.S. Cl. ...................... 435/254.1; 435/148; 435/155; 514/569; 562/462
[58] Field of Search ..................... 435/148, 155, 435/252.1, 254.1, 255.2; 514/569; 562/462

[56] References Cited

FOREIGN PATENT DOCUMENTS

88/03805  6/1988  WIPO .
92/20332  11/1992  WIPO .

OTHER PUBLICATIONS

Gams et al., Compendium of Soil Fungi, vol. 1, Academic Press, London, pp. 7–15 (1980).

Abstract from Report of the J. Chem. Soc. of Japan 77, 305 (1956).

Advances in Neurology, vol. 53 pp. 497–503 (1990).

*Primary Examiner*—David M. Naff
*Attorney, Agent, or Firm*—George W. Johnston; Patricia S. Rocha-Tramaloni

[57] ABSTRACT

Purpurogallin derivatives are produced useful for inhibiting catecholamine-O-methyltransferase. The derivative, 8-O-methylpurpurogallincarboxylic acid, is produced with a microorganism of the genus Absidia having all the identifying characteristics of FERM BP-4599. A pharmaceutical composition containing 8-O-methylpurpurogallincarboxylic acid or an ester or salt thereof is useful in treating Parkinson's diseases.

2 Claims, No Drawings

MICROORGANISM HAVING ALL THE IDENTIFYING CHARACTERISTICS OF ABSIDA FERM BP-4599 FOR PRODUCING PURPUROGALLIN DERIVATIVES

This is a division of application Ser. No. 08/429,457, filed Apr. 27, 1995, now U.S. Pat. No. 5,650,439.

BACKGROUND OF THE INVENTION

1. Field of the Invention

The present invention relates to purpurogallin derivatives useful for inhibiting catecholamine-O-methyl transferase.

2. Background

COMT is an enzyme which catalyzes the transfer of a methyl group from S-adenosyl-L-methionine to the m-hydroxy group of catecholamine transmitters, their metabolites and L-dopa, thereby inactivating them. It is widely distributed in various cerebral and peripheral tissues of all mammalian species. In the cell, the occurrence of at least two distinct isomers of COMT has been demonstrated, of which one is soluble and the other membrane-bound. Although both forms of COMT catalyze the O-methylation of catecholamines, the relative abundance differs in various tissues and species.

Selective COMT inhibitors combined with L-dopa and a peripheral dopa decarboxylase inhibitor are expected to improve the availability and efficiency of L-dopa, by preventing its conversion to 3-O-methyldopa, in L-dopa therapy of Parkinson's disease. Some COMT inhibitors have been described earlier, but all of these have been ineffective, toxic or poorly selective for COMT. Recently, several new potent and selective COMT inhibitors have been developed and are presently under clinical trial for the treatment of Parkinson's disease.

The current situation prompted the inventors to search for further novel COMT inhibitors. For the purpose of finding such novel compounds, the present inventors isolated a number of microorganisms from soils and living things etc., from which the produced compound was purified for study. As the result, the present inventors found that some specific microorganisms produce the novel compound of formula I having a potent and selective COMT inhibiting activity.

SUMMARY OF THE INVENTION

The present invention relates to purpurogallin derivatives, more particularly to 8-O-methylpurpurogallincarboxylic acid of formula (I),

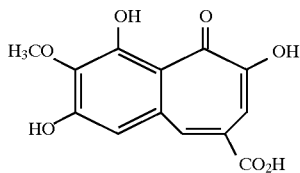

or esters or pharmaceutically acceptable salts thereof. The present invention also relates to a pharmaceutical composition containing 8-O-methylpurpurogallincarboxylic acid of formula (I) or an ester or salt inhibit catecholamine-O-methyltransferase (hereinafter referred to as COMT), and thus are useful in the treatment of Parkinsons diseases, and a process for producing 8-O-methylpurpurogallincarboxylic acid of formula (I) or an ester or salt thereof.

In another aspect, the invention relates to a biologically pure culture of the microorganism of the genus Absidia capable of producing 8-O-methyl-purpurogallincarboxylic acid of formula I.

DETAILED DESCRIPTION OF THE INVENTION

The present invention relates to purpurogallin derivatives, more particularly to 8-O-methylpurpurogallincarboxylic acid of formula (I),

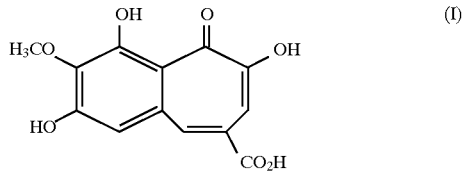

or esters or pharmaceutically acceptable salts thereof. The present invention also relates to a pharmaceutical composition containing 8-O-methylpurpurogallincarboxylic acid of formula (I) or an ester or salt thereof useful for inhibiting catecholamine-O-methyltransferase (hereinafter referred to as COMT), and a process for producing 8-O-methylpurpurogallincarboxylic acid of formula (I) or an ester or salt thereof.

The compound of formula I and esters and pharmaceutically acceptable salts thereof inhibit COMT and thus are useful in the treatment of Parkinson's disease.

The physico-chemical properties of 8-O-methylpurpurogallincarboxylic acid of formula (I) obtained as described in Example 1, herein below, are as follows:

| | |
|---|---|
| Appearance | Brown powder |
| MP | 276–284°C. (dec.) |
| Molecular formula | $C_{13}H_{10}O_7$ |
| HERI-MS (m/z) $M^+$ | |
| calcd. | 278.0426 |
| found | 278.0430 |
| UV $\lambda_{max}$ ($\epsilon$) | |
| in Methanol | 216(17200),285(24200,SH),299(24900), 398(7400) |
| in Methanol + HCl | 219(16900),287(23200),299(23600,SH), 400(5700) |
| in Methanol + NaOH | 230(14600),326(36600),404(4900) |
| IR $v_{max}$ (KBγ) cm$^{-1}$ | 3360,1720,1695,1605,1480,1405,1380, 1255,1010 |
| Solubility | Soluble in Dimethylsulfoxide (DMSO), Methanol Slightly soluble in $H_2O$ |
| $^1$H NMR | |
| (400 MHz, DMSO-$d_6$ with tetramethylsilane (TMS) as an internal standard) δ | 3.87(3H,s),7.05(1H,s),7.51(1H,d,J=1.5Hz), 8.11 (1H,d,3=1.5Hz), 9.75(1H,br), 11.0(1H,br),15.23(1H,s) |
| $^{13}$C NMR | |
| (100 MHz, DMSO-$d_6$ with TMS as an internal standard)δ | 59.7,113.1,113.5,115.2,126.4,134.1,136.9, 137.3,154.1,156.0,158.8,167.5,183.2 |

According to the process of the present invention, 8-O-methylpurpurogallincarboxylic acid of formula (I) or an ester or salt thereof can be produced by cultivating a microorganism belonging to the genus Absidia capable of producing 8-O-methylpurpurogallincarboxylic acid of formula (I) under aerobic condition in a culture medium and isolating said 8-O-methylpurpurogallincarboxylic acid of formula (I) from said culture medium and, if described, converting the resulting compound into an ester or pharmaceutically acceptable salt thereof.

In another aspect, the present invention relates to a biologically pure culture of a microorganism of the genus Absidia having the identifying characteristics of FERM BP-4599. One of its strain characteristics is the production of 8-O-methyl-purpurogallincarboxylic acid of formula I. The microorganisms of the present invention can be any strain (including variants) of the genus Absidia capable of producing 8-O-methyl-purpurogallincarboxylic acid of formula (I). Especially preferred strains are *Absidia sp.* NR7184 as well as variants thereof which can be obtained in any of the ways known for this purpose by one skilled in the art . *Absidia sp.* NR7184 was isolated from a soil sample collected in Mariposa, Calif., U.S.A. and identified as a strain belonging to the genus Absidia.

The strain denoted as *Absidia sp.* NR7184 has been deposited with National Institute of Bioscience and Human-Technology, Agency of Industrial Science and Technology, Japan, under the Budapest Treaty on Mar. 10, 1994 as follows:

*Absidia sp.* NR7184 (FERM BP-4599)

The culture characteristics, taxonomic characteristics and morphological characteristics of *Absidia sp.* NR7184 (FERM BP-4599) are as follows:

Taxonomic characteristics

Taxonomic work was done in accordance with Zycha et al., "Mucorales, eine Beschreibung aller Gattungen und Arten diese Pilzgruppe. Verlag von J. Cramer, Lehre, pp 355 (1969)", O'Donnel "Zygomycetes in culture. University of Georgian, Athens, pp257 (1979)" and Gams et al." Compendium of soil fungi, Vol. 1, Academic Press, London, pp 7–15 (1980).

The colonies were white and grew rapidly on malt extract agar showing a floccose appearance. The stolons were born from the rhizoids. The sporangiophores were formed along the stolons, never from the base of the rhizoids. The pyriform sporangium bearing numerous sporangiospores was supported by a funnel-shaped apophysis with columella, and the sporangial walls remained as short collarettes after maturity. The sporangiospores were minute, smooth-walled and subglobose to oval.

The sporangia were pyriform with a distinct apophysis and were supported terminally on sporangiophores arising along the stolons. On the basis of these distinctive characteristics, the fungal strain was readily included in the genus Absidia in the Mucoraceae of Zygomycotina. Therefore, the strain was identified as *Absidia sp.* NR7184.

The cultivation in accordance with the process of the present invention can be carried out in a culture medium which contains customary nutrients usable by the microorganism being cultivated. As carbon sources there can be mentioned, for example, glucose, sucrose, starch, glycerol, molasses, dextrin and mixtures thereof. Nitrogen sources are, for example, soybean meal, cottonseed meal, meat extract, peptone, dried yeast, yeast extract, cornsteep liquor, ammonium sulfate, sodium nitrate and mixtures thereof. Moreover, there may be added to the culture medium other organic or inorganic substances for promoting the growth of the microorganism and for increasing the production of 8-O-methylpurpurogallincarboxylic acid, examples of such substances being inorganic salts such as, for example, calcium carbonate, sodium chloride, phosphates and the like.

The cultivation is carried out under aerobic conditions in an aqueous medium, preferably by submerged fermentation. The cultivation is suitably carried out at a temperature of 20° C.–35° C., the optimal temperature being 27° C. The cultivation is preferably carried out at a pH of 3 to 9. The cultivation time depends on the conditions under which the cultivation is carried out. In general, it is sufficient to carry out the cultivation for 50–200 hours.

The isolation of 8-O-methylpurpurogallincarboxylic acid from the fermentation broth can be carried out according to known methods. For example, the mycelium can be separated from the fermentation broth by centrifugation or filtration and 8-O-methylpurpurogallincarboxylic acid can be extracted from the filtrate with a water-immiscible organic solvent such as alkanol, for example, n-Butanol and esters, for example, ethyl acetate, butyl acetate and the like. On the other hand, 8-O-methylpurpurogallincarboxylic acid contained in the separated mycelium can be obtained, for example, by extracting the mycelium with a solvent such as aqueous acetone or aqueous methanol, removing the solvent and further extracting the residue with a water-immiscible organic solvent. The thus-obtained solvent phase is dried over a dehydrating agent such as sodium sulfate and the like and then concentrated under reduced pressure. The resulting crude 8-O-methylpurpurogallincarboxylic acid can be purified by means of extraction methods, partition methods, precipitation methods, column-chromatographical methods (using silica gel, reversed-phase silica gel, aluminium oxide, Diaion HP-21 etc. as adsorbents) or by means of molecular sieve methods. The individual active principle can be obtained by means of preparative HPLC methods.

One of ordinary skill in the art can utilize the foregoing procedures to determine whether a strain (including variants of the genus Absidia) is capable of producing 8-O-methyl-purpurogallincarboxylic acid and thus whether such strain would fall within the inventive microorganism.

8-O-methylpurpurogallincarboxylic acid is isolated as free acid, but free 8-O-methylpurpurogallincarboxylic acid can be, if necessary, converted into various pharmaceutically acceptable salts such as the sodium salt, potassium salt and calcium salt by conventional methods. 8-O-methylpurpurogallincarboxylic acid can also be, if desired, converted into esters such as lower alkyl esters, for example, the ethyl or methyl ester, by conventional methods. As used herein, the term lower alkyl, alone or in combination, denotes a straight-or branched-chain alkyl group containing 1 to 5 carbon atoms.

The COMT inhibitory activity of 8-O-methylpurpurogallincarboxylic acid of formula (I) was measured as follows.

The assay mixture (120 $\mu$l) in a mini scintillation vial contained 68 mM K-PO$_4$ buffer (pH 8.0), 10 mM MgCl$_2$, 2.2 mM dithiothreitol, 7.8 U/ml adenosine deaminase, 5 mM EGTA, 100 $\mu$M 1,2-dihydroxybenzene, 183 $\mu$M S-adenosyl-L-[methyl-$^3$H] methionine (73 Ci/mol, Amersham) and human liver enzyme.

In the standard assay, 5 $\mu$l of inhibitor was added to the incubation mixture and the reaction was started with the supplementation of crude enzyme (8.3 $\mu$g protein) prepared from human liver. After incubation at 37° C. for 30 minutes, the reaction was stopped by immersion of the vials in ice water. 100 $\mu$l of 1M guaiacol HCl was added and the samples were extracted with 2 ml of a scintillation cocktail of hexane/toluene (4:1). The radioactivity of O$^3$H-methylated products were measured by a liquid scintillation counter (LSC1100, Aloka).

Inhibitory activities of 8-O-methylpurpurogallincarboxylic acid and reference compounds are shown in the following Table.

TABLE

| Compound | $IC_{50}$ ($\mu$M) |
|---|---|
| 8-O-methylpurpurogallincarboxylic acid | 2.23 |
| Tropolone | 963 |
| Propyl gallate | 0.455 |

Acute toxicity of 8-O-methylpurpurogallincarboxylic acid was not observed.

The novel 8-O-methylpurpurogallincarboxylic acid and its salts and esters of the present invention can find use as medicaments, for example in the form of unit dose pharmaceutical preparations which contain them in admixture with an organic or inorganic inert carrier material suitable for enteral application, such as gelatin, gum arabic, lactose, starch, magnesium stearate, talc, vegetable oils, polyalkylene glycols. The unit dose pharmaceutical preparations can be present in solid form, for example, as tablets, coated tablets, dragees or capsules, hard gelatin or soft gelatin, or in liquid form, for example, as solutions, syrups, or suspensions.

A dose unit may contain 10 to 200 mg of active ingredient. The daily dosage for an adult can be in the range from 10 to 400 mg and may be varied according to individual requirements which can be determined by those of ordinary skill in the art.

The following example further illustrates the present invention.

EXAMPLE 1

A portion of the stock culture (100 $\mu$l) of *Absidia sp.* NR7184 (FERM-BP No. 4599) preserved at $-80°$ C. was inoculated into a 500-ml Erlenmeyer flask containing 100 ml of a medium consisting of 2% glucose, 2% potato starch, 2% toast soya, 0.5% yeast extract, 0.25% NaCl, 0.005% $ZnSO_4.7H_2O$, 0.0005% $CuSO_4.5H_2O$, 0.0005% $MnSO_4.4H_2O$, 0.32% $CaCO_3$ and 0.03% Nissan disfoam CA-115. The pH of the medium was adjusted to 7.0 prior to addition of calcium bicarbonate. This seed culture was shaken on a rotary shaker at 220 rpm at 27° C. for 3 days. Then 2 ml aliquots were transferred into fifty 500-ml flasks containing the same medium and incubated under the same conditions for a further 6 days.

The culture broth (10 liters) was separated into filtrate and mycelium by centrifugation. The culture filtrate (6.1 liters) was extracted with butanol (6.1 liters) at pH 2. The mycelial cake was extracted with 2.5 liters of ethanol. After removal of the mycelial cake, the ethanol- extract was concentrated under reduced pressure to dryness and dissolved in water (2 liters). The aqueous solution was extracted with butanol (2 liters) at pH 2. Both butanol extracts were combined and concentrated under reduced pressure. The concentrate (32.0 g) was dissolved in water (1 liter) and subjected to a column chromatography on Diaion HP-21 (100 ml) (Mitsubishi Chemical Industries Ltd.) using water and acetone as eluents. The active fractions were combined and concentrated under reduced pressure. The concentrate was subjected to a column chromatography on Sephadex LH-20 (1 liter) (Pharmacia) using methanol as eluent. The active fractions were combined and concentrated under reduced pressure. The concentrate was dissolved in water (30 ml) and subjected to a column chromatography on Bond elute $C_{18}$ (Varian Sample Preparation Products) using water and methanol as eluents. The active fractions were combined and concentrated under reduced pressure. 8-O-methylpurprogallincarboxylic acid was purified by preparative HPLC under the following conditions followed by ethyl acetate extraction at pH2; column: Capcellpak $C_{18}$ (20×250 mm), solvent: methanol-0.1M aq. $NaH_2PO_4$=1:1 (pH2.2), flow rate: 10 ml/minute; detection: UV 260 nm. 8-O-methylpurprogallincarboxylic acid (14 mg) was obtained as a brown amorphous powder.

The following example illustrates a pharmaceutical preparation containing 8-O-methylpurpurogallincarboxylic acid of the present invention:

EXAMPLE 2

Tablets each containing the following ingredients were manufactured in a conventional manner:

| | |
|---|---|
| 8-O-methylpurpurogallincarboxylic acid | 100 mg |
| Starch | 26 mg |
| Carboxymethylcellulose calcium | 15 mg |
| Crystalline cellulose | 20 mg |
| magnesium stearate | 4 mg |
| | 165 mg |

I claim:

1. A biologically pure culture of the microorganism of the genus Absidia, having all the identifying characteristics of FERM BP-4599.

2. A biologically pure culture of the microorganism, *Absidia sp.* NR 7184, having deposit number FERM BP-4599.

* * * * *